United States Patent [19]

Van Gemert et al.

[11] Patent Number: 5,395,567
[45] Date of Patent: Mar. 7, 1995

[54] PHOTOCHROMIC SPIRONAPHTHOPYRAN COMPOUNDS

[75] Inventors: Barry Van Gemert, Murrysville; David B. Knowles, Apollo, both of Pa.

[73] Assignee: PPG Industries, Inc., Pittsburgh, Pa.

[21] Appl. No.: 228,807

[22] Filed: Apr. 18, 1994

[51] Int. Cl.$^6$ .................. C07D 311/92; C07D 311/96
[52] U.S. Cl. .................. 252/586; 252/589; 549/330; 524/110
[58] Field of Search ............... 549/330; 252/586, 589; 524/110

[56] References Cited

U.S. PATENT DOCUMENTS

| | | | |
|---|---|---|---|
| 3,567,605 | 3/1971 | Becker | 204/158 |
| 3,627,690 | 12/1971 | Cassella et al. | 252/300 |
| 4,563,458 | 1/1986 | Widdig et al. | 514/253 |
| 4,818,096 | 4/1989 | Heller et al. | 351/163 |
| 4,826,977 | 5/1989 | Heller et al. | 544/70 |
| 4,931,221 | 6/1990 | Heller | 252/586 |
| 4,980,089 | 12/1990 | Heller | 252/586 |
| 4,990,287 | 2/1991 | Bennion et al. | 252/586 |
| 5,066,818 | 11/1991 | Van Gemert et al. | 549/389 |
| 5,200,116 | 4/1993 | Heller | 252/586 |
| 5,238,981 | 8/1993 | Knowles | 524/99 |
| 5,244,602 | 9/1993 | Van Gemert | 252/589 |
| 5,274,132 | 12/1993 | Van Gemert | 549/389 |
| 5,330,686 | 7/1994 | Smith et al. | 252/586 |

FOREIGN PATENT DOCUMENTS

294056 12/1988 European Pat. Off. .
562915A 9/1993 European Pat. Off. .

OTHER PUBLICATIONS

Padwa et al., "Photochemical Ring-Opening Reactions of Substituted Chromenes and Isochromenes", J. Org. Chem., vol. 40, No. 8, 1975, pp. 1142-1149.

Irving et al, "Styrylpyrylium Salts, Part XII.", JACS, vol. 1929, pp. 1093-1095.

Hirschberg and Fischer, "Photochromism and Reversible Multiple Internal Transitions in some spiroPyrans at Low Temperatures, Part II.", JACS, vol. 1954, pp. 3129-3137.

*Primary Examiner*—C. Warren Ivy
*Assistant Examiner*—A. A. Owens
*Attorney, Agent, or Firm*—Irwin M. Stein

[57] ABSTRACT

A novel photochromic spironaphthopyran composition having the general structural formula:

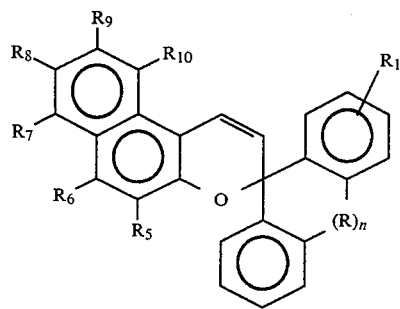

in which phenyl substituents positioned adjacent to the oxygen of the pyran ring are linked at their adjacent ortho positions by the functionality $(R)_n$ wherein n is the integer 0-2 and wherein R is methylene ($-CH_2-$), vinylene ($-C=C-$), or a carbon-carbon bond, i.e., when n is 0. The groups $R_1$ and $R_5-R_{10}$ may be hydrogen or a variety of substituents.

15 Claims, No Drawings

PHOTOCHROMIC SPIRONAPHTHOPYRAN COMPOUNDS

FIELD OF THE INVENTION

The invention relates to certain novel spironaphthopyran compounds, and more particularly relates to certain photochromic spironaphthopyran compounds for use in plastic ophthalmic lenses or other related articles.

BACKGROUND OF THE INVENTION

Photochromic plastic materials, particularly plastic materials for optical applications, have in recent years attracted growing commercial interest due to their light weight in comparison to glass. Generally, these optical plastics incorporate organic photochromic compounds. When exposed to light radiation containing ultraviolet (UV) rays, such as the ultraviolet radiation in sunlight or the light of a mercury lamp, these photochromic compounds exhibit a reversible change in color. When the ultraviolet radiation is discontinued, the photochromic compound returns to its original color or colorless state. Ideal photochromic compounds for use in plastic optical applications change color efficiently upon exposure to near ultraviolet light, resist bleaching in white light and have a relatively fast fade rate.

A variety of organic photochromic compounds are already known in the art. U.S. Pat. No. 3,567,605 to Becker describes a series of pyran derivatives, including certain benzopyrans and naphthopyrans. U.S. Pat. No. 4,563,458 describes chroman and chromene compounds intended for use in pharmaceutical compositions. European Patent Publication 246, 114 and U.S. Pat. No. 4,826,977 describe a series of photochromic spiropyrans in which an adjacent group is attached at the position adjacent to the oxygen in the pyran ring. U.S. Pat. No. 4,818,096 and European Patent Publication 250,193 describe photoreactive plastic lenses that are coated or impregnated with the photochromic spiropyrans of European Patent Publication 246,114 in combination with a blue photochromic benzopyran or naphthopyran having an aminophenyl substituent at the position adjacent to the oxygen in the pyran ring. European Patent Publication 294,056 describes a process for producing a polyurethane plastic having photochromic properties wherein the photochromic compounds described include, among others, a naphthopyran derivative in which the pyran ring is substituted at the position adjacent to the oxygen in the pyran ring with di(p-methoxyphenyl) substituents.

Padwa et al. in *J. Org. Chem.*, Volume 40, No. 8, 1975, page 142, describes the investigation of photochemical reactions of 2,2-dimethylbenzopyran and related compounds, identifies fatigue products and suggests pathways to the ring-opened colored intermediates and the phenolic degradation products.

Notwithstanding the existence of a number of known organic photochromic compounds, the extent of the photochromicity characteristic among various organic compounds has yet to be completely investigated. Further identification of new organic photochromic compounds is of value to the ophthalmic lens and related industries because, for example, different photochromic compounds can have vastly different physical properties other than photochromicity and therefore may well have particular advantages in certain applications. A need therefore remains to identify novel compounds which, among their other properties, are photochromic.

SUMMARY OF THE INVENTION

The present invention is directed to novel photochromic spironaphthopyran compounds, more particularly photochromic spironaphthopyrans having the general graphic formula:

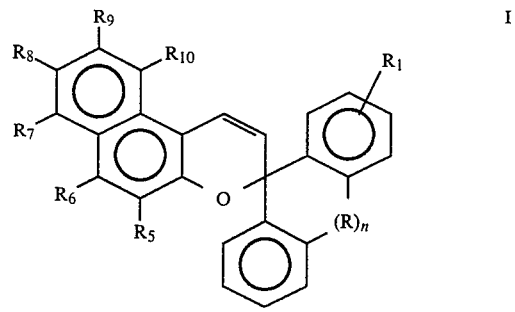

in which the phenyl substituents, positioned adjacent to the oxygen of the pyran ring are linked at their adjacent ortho positions by the functionality $(R)_n$ wherein n is an integer of from 0-2, provided that when R is the methylene group ($-CH_2-$), n is an integer of from 1-2, and when R is ethenylene (vinylene), $-CH=CH-$, n is 1. When n is 0, the two phenyl groups are linked by a carbon-carbon bond. The substituents $R_i$ and $R_5-R_{10}$ may be a wide variety of groups, as described in more detail herein.

DETAILED DESCRIPTION OF THE INVENTION

The present invention is directed to the novel spironaphthopyrans of graphic formula I in which the phenyl groups positioned adjacent to the oxygen of the pyran ring are linked at their adjacent ortho positions by the functionality, $(R)_n$, wherein n is an integer of from 0-2 and R is selected from the groups methylene ($-CH_2-$), vinylene ($-CH=CH-$) and a carbon-carbon bond; provided further that when R is $-CH_2-$, n equals 1-2, when R is $-C=C-$, n equals 1, and when n equals 0, R is a carbon-carbon bond. The substituents $R_1$ and $R_5-R_{10}$ may be a wide variety of groups. These novel spironaphthopyrans have photochromic properties.

The article "Styrylpyrylium salts—part XII," *Journal of the Chemical Society*, Vol. 1929, pp. 1093–1095, by Irving et al., discloses xantha β-naphthaspiropyran, which differs from the compounds of the present invention in that the two phenyl groups of the diaryl moiety are linked by an oxygen, not by the group, R, as defined herein. Notably, the Irving article does not address photochromicity but rather describes thermochromism. Hirschberg and Fischer in *Journal of the Chemical Society*, Vol. 1954, pp. 3129–3137, describes Irving's xantha β-naphthaspiropyran as being photochromic as well as thermochromic. However, neither group of authors addresses the photochromism of the compounds of the present invention.

Apart from the functional, e.g., aliphatic, group or bond which links the two phenyl groups of the spironaphthopyrans of the present invention, one of the two phenyl groups may be additionally substituted with the group ($R_1$), wherein $R_1$ may be a ($C_1$-$C_5$) alkyl, ($C_1$-$C_5$) alkoxy, hydrogen, or halogen (fluoro and chloro being preferred). This substitution specifically increases the bathochromic shift of the colored form of the compound when it is an electron donating group, such as alkyl or more desirably, alkoxy. The spironaphthopyrans of the present invention generally color to a yellow-to-orange color when activated, with the more extensively substituted compounds exhibiting the bathochromic shift to orange.

The naphthyl portion of the spironaphthopyrans of graphic formula I may optionally be substituted with the substitutents $R_5$–$R_{10}$. In such event each of the $R_5$–$R_{10}$ substituents may be chosen from the group consisting of $C_1$–$C_{10}$ straight and branched chain alkyl, $C_5$–$C_7$ cycloalkyl, phenyl, mono- or di-substituted phenyl, $C_1$–$C_4$ alkoxy, carboxy, $C_1$–$C_4$ carboxyalkyl, acetoxy, benzyloxy, halogen, i.e., chlorine, fluorine, bromine and iodine, acrylyl, methacrylyl, acryloxy ($C_1$–$C_4$) alkyl, and methacryloxy ($C_1$–$C_4$) alkyl. When $R_5$–$R_{10}$ are not one of the aforesaid groups, they are hydrogen. The aforedescribed mono- and di-substituted phenyl substituent(s) each may be selected from the group consisting of $C_1$–$C_4$ alkyl, $C_1$–$C_4$ alkoxy, chloro and fluoro. Preferably, the phenyl group is mono-substituted and that substituent is in the para position, e.g., p-methyl phenyl, p-chloro phenyl and p-methoxy phenyl. Still more particularly, the $R_5$–$R_{10}$ substituents each may be hydrogen, $C_1$–$C_3$ alkyl, $C_1$–$C_3$ alkoxy, chloro, fluoro, phenyl and $C_1$–$C_3$ alkoxyphenyl, e.g., p-methoxy phenyl. Preferably, the naphthyl portion of the spironaphthopyran is substituted with one or two substituent groups, i.e., one or two of the substituents $R_5$, $R_6$, $R_7$, $R_8$, $R_9$ and $R_{10}$ are not hydrogen and are selected from the aforedescribed enumerated substituents. More preferably, the substituents that are other than hydrogen are chosen from $R_5$, $R_8$ and $R_9$, and still more preferably, the substituents that are other than hydrogen are $R_8$ and $R_9$.

Although specific preparations for certain of the spironaphthopyrans of the present invention appear in the Examples below, generally the spironaphthopyrans are synthesized as follows. An appropriately substituted or unsubstituted cyclic ketone (9-fluorenone, anthrone, dibenzosuberone, or dibenzosuberenone are preferred) is reacted by stirring with sodium acetylide in an organic solvent in a reaction flask for 20–40 hours with stirring. The reaction mixture is then quenched in ice water and the organic reaction product extracted, dried and separated. The resulting acetylenic alcohol is then further reacted, with the application of heat, with an appropriately substituted naphthol in the presence of an acid catalyst. After a reaction time of a few to several hours, the reaction mixture is quenched in aqueous sodium hydroxide and the resulting spironaphthopyran product is separated from the associated organic layer.

The present spironaphthopyrans are suitable for use in any application in which organic photochromic substances may be employed, such as optical lenses, e.g., ophthalmic and plano lenses, face shields, goggles, ski goggles, visors, camera lenses, windows, automotive windshields, aircraft and automotive transparencies, e.g., T-roofs, sidelights and backlights, plastic films and sheets, textiles and coatings, e.g., coating compositions such as paints, and verification marks on security documents, e.g., documents such as banknotes, passports and drivers' licenses for which authentication or verification of authenticity may be desired.

Commercially available photoreactive glass lenses containing silver halide particles darken to a gray or brown color in sunlight. In order to achieve a similar gray or brown color on exposure to ultraviolet light, it is contemplated that the present spironaphthopyrans be used in combination with other appropriate complementary organic photochromic materials. For example, a compound which colors to yellow in its activated form may be blended with a compound that colors to an appropriate purple to produce a brown shade. Similarly, a compound which is orange in its colored state will produce a shade of gray when used in conjunction with an appropriate blue coloring compound. The aforesaid described combination of photochromic materials may be used also in applications other than photochromic lenses.

Particularly contemplated classes of complementary organic photochromic compounds that may be used in combination with the naphthopyrans of the present invention include: purple/blue spiro(indolino) benzoxazines, such as those described in U.S. Pat. No. 4,816,584; spiro(indolino) pyridobenzoxazine photochromic compounds, such as those described in U.S. Pat. No. 4,637,698; and spiro(indoline) naphthoxazines, such as those described in U.S. Pat. Nos. 3,562,172, 3,578,602, 4,215,010 and 4,342,668. All of the aforedescribed organic photochromic compounds are reported to exhibit a color change of from colorless to purple/blue on exposure to ultraviolet light. The disclosures of said U.S. patents are hereby incorporated herein in by reference.

Other contemplated complementary organic photochromic compounds that are reported to exhibit a color change of from colorless to yellow/orange when exposed to UV light may be used in combination with the naphthopyran compounds of the present invention to augment the yellow/orange color of those activated photochromic compounds. Such complementary yellow/orange compounds include: benzopyrans and naphthopyrans having a spiro adamantylene group in the 2-position of the pyran ring, such as those described in U.S. Pat. No. 4,826,977, and naphthopyran compounds such as those described in U.S. Pat. No. 5,066,818. The disclosures of such U.S. patents are also hereby incorporated herein, in toto, by reference.

The naphthopyran compounds of the present invention may be used in admixture with or in conjunction with the aforedescribed complementary or augmenting organic photochromic compounds in amounts and in a ratio such that an organic host material to which the mixture of photochromic compound(s) is applied or in which they are incorporated exhibit a substantially neutral color when activated with unfiltered sunlight, i.e., as near a neutral gray or brown color as is possible given the colors of the activated photochromic compounds. The relative amounts of the photochromic compounds used will vary and depend in part upon the relative intensities of the color of the activated species of such compounds.

For example, the naphthopyran compounds of the present invention may be combined with one or more of the aforedescribed purple/blue spirooxazine- and/or pyran-type organic photochromic compounds in amounts and in ratios such that an organic host material to which the mixture of compounds is applied or in which they are then incorporated exhibits a near-brown color. Generally, the weight ratio of each of the aforedescribed spirooxazine- and pyran-type compound(s) to the naphthopyran compound(s) of the present invention will vary from about 1:3 to about 3:1, e.g., between about 1:2 or 0.75:1 and about 2:1.

A near neutral gray color exhibits a spectrum that has relatively equal absorption in the visible range between 400 and 700 nanometers, e.g., between 440 and 660 nanometers. A near neutral brown color exhibits a spectrum in which the absorption in the 400–550 nanometer range is moderately larger than in the 550–700 nanometer range. An alternative way of describing color is in terms of its chromaticity coordinates, which describe the qualities of a color in addition to its luminance factor, i.e., its chromaticity. In the CIE system, the chromaticity coordinates are obtained by taking the ratios of the tristimulus values to their sum, e.g., $x = X/X+Y+Z$ and $y = Y/X+Y+Z$. Color as described in the CIE system can be plotted on a chromaticity diagram, usually a plot of the chromaticity coordinates x and y. See pages 47–52 of *Principles of Color Technology*, by F. W. Billmeyer, Jr. and Max Saltzman, Second Edition, John Wiley and Sons, N.Y. (1981).

The amount of photochromic substance or composition containing it applied to or incorporated into a host material is not critical provided that a sufficient amount is used to produce a photochromic effect discernible to the naked eye. Generally such amount can be described as a photochromic amount. The particular amount used depends often upon the intensity of color desired upon irradiation thereof and upon the method used to incorporate or apply the photochromic substance. Typically, the more compound applied or incorporated, the greater is the color intensity.

Generally, the amount of each photochromic substance incorporated into or applied to the host material may range from about 0.01 or 0.05 to about 10 to 20 percent by weight. More typically, the amount of photochromic substance(s) incorporated into or applied to the host material will range from about 0.01 to about 2 weight percent, more particularly, from about 0.01 to about 1 weight percent, e.g., from about 0.1 or 0.5 to about 1 weight percent, based on the weight of the host material. Expressed differently, the total amount of photochromic substance incorporated into or applied to an optical host material may range from about 0.15 to about 0.35 milligrams per square centimeter of surface to which the photochromic substance(s) is incorporated or applied.

Photochromic compounds of the present invention, mixtures of such compounds with other photochromic compounds, or compositions containing the same may be applied to or incorporated into a host material by various methods described in the art. Such methods include: dissolving or dispersing the photochromic substance within the host material, e.g., immersion of the photochromic substance into the host material by immersion of the host material in a hot solution of the photochromic substance or by thermal transfer; providing the photochromic substance as a separate layer between adjacent layers of the host material, e.g., as a part of a polymer film; and applying the photochromic substance as part of a coating placed on the surface of the host material. The term "imbibition" or "imbibe" is intended to embrace, nonexclusively, permeation of the photochromic substance alone into the host material, solvent assisted transfer absorption of the photochromic substance into a porous polymer, vapor phase transfer, and other such transfer mechanisms. See U.S. Pat. No. 5,066,818, Column 14, line 41 to Column 15, line 25 for examples of the above methods.

The polymer host material will usually be transparent, but may be translucent or even opaque. The polymer product need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Further, the resin color should not be such that it masks the color of the activated form of the photochromic substance, i.e., so the change in color is readily apparent to the observer. Preferably, the host material article is a solid transparent or optically clear material.

Compatible (chemically and color-wise) tints, i.e., dyes, may be applied to the host material to achieve a more aesthetic result, for medical reasons, or for reasons of fashion. The particular dye selected will vary and will depend on the aforesaid need and result to be achieved. In one embodiment, the dye may be selected to complement the color resulting from the activated photochromic substances, e.g., to achieve a more neutral color or to absorb a particular wavelength of incident light. In another embodiment, the dye may be selected to provide a desired hue to the host matrix when the photochromic substance is in an unactivated state.

Typically, tinting is accomplished by immersion of the host material in a heated aqueous dispersion of the selected dye. The degree of tint is controlled by the temperature of the dye bath and the length of time the host material is allowed to remain in the bath. Generally, the dye bath is at temperatures of less than 100° C., e.g., from 70° C. to 90° C., such as 800° C., and the host material remains in the bath for less than five (5) minutes, e.g., between about 0.5 and 3 minutes, e.g., about 2 minutes. The degree of tint is such that the resulting article exhibits from about 70 to 85 percent, e.g., 80–82 percent, light transmission.

Adjuvant materials may also be incorporated into the host material with the photochromic substances prior to, simultaneously with or subsequent to application or incorporation of the photochromic substances in the host material. For example, ultraviolet light absorbers may be admixed with photochromic substances before their application to the host material or such absorbers may be superimposed as a layer between the photochromic substance and the incident light. Further, stabilizers may be admixed with the photochromic substances prior to their application to the host material to improve the light fatigue resistance of the photochromic substances. Stabilizers, such as hindered amine light stabilizers and singlet oxygen quenchers, e.g., a nickel ion complex with an organic ligand, are contemplated. They may be used alone or in combination in stabilizing amounts. Such stabilizers are described in U.S. Pat. No. 4,720,356. Finally, appropriate protective coating(s) may be applied to the surface of the host material. These may be abrasion resistant coatings and/or coatings that serve as oxygen barriers. Such coatings are known in the art.

Singlet oxygen quenchers that may be used as stabilizers include complexes of nickel $(2+)$, i.e., $Ni^{2+}$, with an organic ligand, cobalt (III) tris-di-n-butyldithiocarbamate, cobalt (II) diisopropyldithiocarbamate, and nickel diisopropyldithiophosphate. Such singlet oxygen quenchers are used in stabilizing amounts.

Preferred are complexes of $Ni^{2+}$ such as [2,2-thiobis[4-(1,1,3,3-tetramethylbutyl)phenolato](butylamine)]nickel, which is sold under the tradename of CYASORB UV 1084; nickel [O-ethyl(3,5-di-tert-butyl-4-hydroxybenzyl)]phosphonate, which is sold under the tradename IRGASTAB 2002; nickel dibutyldithiocarbamate, which is sold under the tradename RYLEX NBC; bis[2,2'-thiobis-4-(1,1,3,3-tetramethylbutyl)phenolato]nickel, which is sold under the tradename UV-CHEK AM 101; nickel diisopropyldithiophosphate and other $Ni^{2+}$ complexes sold under the tradenames of UV-CHEK AM 105, UV-CHEK 126, and UV-CHEK AM 205.

Hindered amine light stabilizers that may be used include bis(2,2,6,6-tetramethyl-4-piperidinyl) sebacate, which is sold under tradename TINUVIN 770; bis(1,2,2,6,6-pentamethyl-4-piperidinyl) sebacate, which is sold under the tradename TINUVIN 765; di(1,2,2,6,6-pentamethyl-4-piperidinyl)butyl-(3',5'-ditertiary-butyl-4-hydroxybenzyl)malonate, which is sold under the tradename TINUVIN 144; poly[(6[-(1,1,3,3-tetramethylbutyl)amino]-1,3,5-triazine-2,4-diyl)-(6-[2,2,6,6-tetramethyl-4 -piperidinyl]-amino-hexamethylene)], which is sold under the tradename CHIMASSORB 944; and poly[[6-(morpholino)-s-triazine-2,4-diyl][16-(2,2,6,6-tetramethyl-4-piperdyl)amino]hexamethylene], which is sold under the tradename CYASORB 3346. Other hindered amine light stabilizers that may be used are those sold under the tradename TINUVIN 622, SPINUVEX A-36 and HOSTAVIN TMN 20. Such stabilizers are used in stabilizing amounts.

The foregoing singlet oxygen quenchers and hindered amine light stabilizers may be used singly or in combination in amounts sufficient to enhance the light-fatigue resistance of the photochromic substance(s) described herein. Between 0.01 and about 5 percent by weight of the foregoing stabilizers may be used (alone or in combination) to improve the light fatigue resistance of the photochromic materials.

The polymer host material will usually be transparent, but may be translucent or even opaque. The polymer product need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Further, the resin color should not be such that it masks the color of the activated form of the photochromic substance, i.e., so the change in color is readily apparent to the observer. Preferably, the host material article is a solid transparent or optically clear material, e.g., materials suitable for optical applications, such as plano and ophthalmic lenses, windows, automotive transparencies, e.g., windshields, aircraft transparencies, plastic sheeting, etc.

Examples of host materials which may be used with the photochromic substances or compositions described herein include: polymers, i.e., homopolymers and copolymers, of polyol (allyl carbonate) monomers, polymers, i.e., homopolymers and copolymers, of polyfunctional acrylate monomers, polyacrylates, poly(alkylacrylates) such as poly(methyl methacrylate), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, polycarbonates, poly(ethylene terephthalate), polystyrene, copoly(styrene-methyl methacrylate), copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers.

Transparent copolymers and blends of transparent polymers are also suitable as host materials. Preferably, the host material is an optically clear polymerized organic material prepared from a polycarbonate resin, such as the carbonate-linked thermoplastic resin derived from a bisphenol, such as bisphenol A, and phosgene, which is sold under the trademark LEXAN. A poly(methyl methacrylate), such as the material sold under the trademark PLEXIGLAS; polymerizates of a polyol (allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis(allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain alkyl and/or acrylyl functional groups, as described in U.S. Pat. No. 5,200,483; cellulose acetate, cellulose propionate, cellulose butyrate, cellulose acetate butyrate, polystyrene and copolymers of styrene with methyl methacrylate, vinyl acetate and acrylonitrile.

Polyol (allyl carbonate) monomers which may be polymerized to form a transparent thermoset host material are the allyl carbonates of linear or branched aliphatic or aromatic liquid polyols, e.g., aliphatic glycol bis(allyl carbonate) compounds, or alkylidene bisphenol bis(allyl carbonate) compounds. These monomers can be described as unsaturated polycarbonates of polyols, e.g., glycols. The monomers can be prepared by procedures well known in the art, e.g., methods described in U.S. Pat. Nos. 2,370,567 and 2,403,113.

Although not intended to be limiting, the following examples are helpful in describing various aspects of the present invention.

EXAMPLE 1

In order to prepare a composition according to the present invention in which R is a carbon-carbon bond and $R_1$ and $R_5$–$R_{10}$ are hydrogen, the following procedure was followed. Five (5.0) grams of 9-fluorenone (0.028 mole) was added to 200 milliliters (mls) of tetrahydrofuran and 9.0 grams of an 18 percent suspension of sodium acetylide (0.033 moles) in xyleneomineral oil was slowly added to the solution with stirring. After 32 hours at room temperature, the reaction mixture was quenched in 200 mls of ice water. After stirring for 30 minutes, the mixture was extracted with 3–100 mls portions of diethyl ether. The organic layers were combined and dried over anhydrous magnesium sulfate. The solvent, a mixture of tetrahydrofuran and diethyl ether, was removed under vacuum to yield 5.7 grams of an oil containing 9-ethinyl-9-hydroxyfluorene. The oil was not purified further but was added to 200 mls of benzene containing 2.5 grams of 2-naphthol. A catalytic amount of p-toluenesulfonic acid was added to the stirred solution. The reaction was heated between 30° and 35° C. for 5 hours before being quenched in a 10 weight percent aqueous solution of sodium hydroxide. The organic layer was separated and the solvent, benzene, removed under vacuum. The residue was chromatographed on a silica gel column using 50-50 ethyl acetate and hexane as the eluent. The photochromic fractions were collected and the solvent removed under vacuum to yield 1.0 gram of product having a melting point of 216°–218° C. A nuclear magnetic resonance (NMR) spectrum of the recovered product showed it to have a structure consistent with the desired product, which may be graphically depicted as:

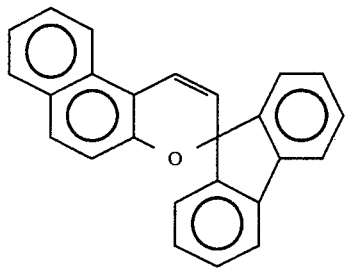

or Spiro[3H-naphtho[2,1-b]pyran-3-9'-fluorene].

EXAMPLE 2

The preparation of the following graphically depicted compound:

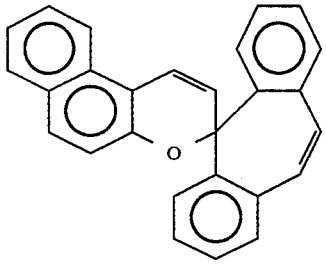

or Spiro[3H-naphtho[2,1-b]pyran-3-5'-dibenzosuberene], in which R in graphic formula I is —C=C—(vinylene), and $R_1$ and $R_5$-$R_{10}$ are hydrogen was conducted by following the process of Example 1 except for substituting a stoichiometrically equivalent amount of dibenzosuberenone for the 9-fluorenone. The recovered product had a melting point of 182°–184° C.

EXAMPLE 3

Example 1 was repeated, but instead of using unsubstituted 2-naphthol a stoichiometrically equivalent amount of 6-methoxy-2-naphthol was used. The resultant spironaphthopyran can be represented by the structural formula:

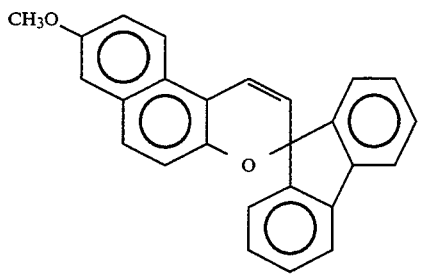

or 8-methoxy-spiro-[3H-naphtho[2,1-b]pyran-3-9'-fluorene]. The product had a melting point of 223° C.

EXAMPLE 4

The compounds prepared according to Examples 1, 2 and 3 were evaluated for photochromicity by dissolving each in ethyl cellulose polymer and depositing a thin layer of the resultant polymer onto a glass slide, as follows: 150 milligrams (mg) of the compound was dissolved in 10 grams of a 10 weight percent solution of ethyl cellulose in toluene. A thin even film of the resulting solution was spread on a glass slide using an 8 mil draw down bar. The films were dried to remove the toluene leaving a film of ethyl cellulose containing the photochromic compound.

The slides prepared as described above were tested for photochromic response rates on an optical bench. The samples were illuminated by a 150 watt Xenon lamp fitted with a copper sulfate bath and a neutral density filter at an intensity of about one sun. A second beam of light provided by a filtered tungsten lamp arranged to pass through the sample area exposed by the UV source was used to monitor changes in transmission of the sample over different wavelength ranges in the visible region of the spectrum. The intensity of the monitoring beam after passing through the sample was measured by means of an IL-1500 radiometer equipped with a silicon detector head and matching filters.

Test values obtained appear in Table 1. The delta (Δ) OD/Min, which represents the sensitivity of the photochromic compound's response to ultraviolet light, was measured using photopic filters on the silicon detector. The response of the filtered detector approximated the luminosity curve. The delta OD/Min was measured over the first five (5) seconds of UV exposure, then expressed on a per minute basis. The delta OD @ Saturation was taken under identical conditions as the delta OD/Min, except UV exposure was continued until no further delta OD could be detected. Lambda max is the wavelength in the visible spectrum at which the maximum absorption of the activated (colored) form of the photochromic compound in ethyl cellulose occurs. The Bleach Rate T ½ is the time interval in seconds for the absorbance of the activated form of the naphthopyran in the test polymers to reach one half the highest absorbance at room temperature (72° F., 22.2° C.) after removal of the source of activating light.

| COMPOUND EXAMPLE | LAMBDA MAX | DELTA OD/MIN SENSITIVITY | DELTA OD @ SATURATION | BLEACH RATE T½ (Sec.) |
|---|---|---|---|---|
| 1 | 460 nm | 0.90 | 0.50 | 360 |
| 2 | 437 nm | 0.90 | >1.0 | >600 |

-continued

| COMPOUND EXAMPLE | LAMBDA MAX | DELTA OD/MIN SENSITIVITY | DELTA OD @ SATURATION | BLEACH RATE T½ (Sec.) |
|---|---|---|---|---|
| 3 | 488 nm | 0.55 | 1.01 | >1200 |

Although the present invention has been described with reference to the specific details of particular embodiments thereof, it is not intended that such details be regarded upon the scope of the invention except insofar as they are included in the accompanying claims.

We claim:

1. A spironaphthopyran representable by the graphic formula:

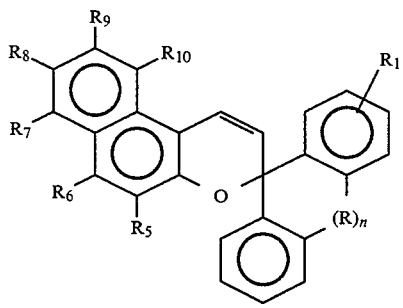

wherein n is an integer of from 0 to 2, R is selected from methylene and vinylene when n is 1, is methylene when n is 2, and is a carbon-carbon bond when n is 0, $R_1$ is hydrogen, $C_1-C_5$ alkyl, $C_1-C_5$ alkoxy or halogen, and $R_5-R_{10}$ are each selected from hydrogen, $C_1-C_{10}$ alkyl, $C_5-C_7$ cycloalkyl, phenyl, mono- or di-substituted phenyl, $C_1-C_4$ alkoxy, carboxy, $C_1-C_5$ carboxyalkyl, acetoxy, benzyloxy, halogen, acrylyl, methacrylyl, acryloxy ($C_1-C_4$) alkyl, or methacryloxy ($C_1-C_4$) alkyl, said phenyl substituents being selected from $C_1-C_4$ alkyl, $C_1-C_4$ alkoxy, chloro and fluoro.

2. The spironaphthopyran of claim 1 wherein $R_6$, $R_7$ and $R_{10}$ are hydrogen.

3. The spironaphthopyran of claim 1 wherein $R_5$, $R_6$, $R_7$ and $R_{10}$ are hydrogen.

4. The spironaphthopyran of claim 3 wherein $R_1$, is hydrogen.

5. The spironaphthopyran of claim 1 wherein $R_5-R_{10}$ are each selected from hydrogen, $C_1-C_3$ alkyl, $C_1-C_3$ alkoxy, chloro, fluoro, phenyl and $C_1-C_3$ alkoxyphenyl, and the halogen of $R_1$ is fluorine or chlorine.

6. The spironaphthopyran of claim 5 wherein $R_6$, $R_7$ and $R_{10}$ are hydrogen.

7. The spironaphthopyran of claim 6 wherein $R_1$ is hydrogen.

8. The spironaphthopyran of claim 1 wherein the spironaphthopyran is selected from the group consisting of 8-methoxy-spiro-[3H-naphtho[2,1-b]pyran-3-9'-fluorene], Spiro[3H-naphtho[2,1-b]pyran-3-5'-dibenzosuberene] and Spiro[3H-naphtho[2,1-b]pyran-3-9'-fluorene].

9. A photochromic article comprising an organic host material and a photochromic amount of a photochromic spironaphthopyran of claim 1.

10. The photochromic article of claim 9 wherein the organic host material is selected from the group consisting of polyacrylates, cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonate, polyurethane, poly(ethylene terephthalate), polystyrene, copoly(styrene-methyl methacrylate), copoly(styrene-acrylonitrile), polyvinylbutyral, and polymers prepared from polyol (alkyl carbonate) monomers, polyfunctional acrylate monomers and diallylidene pentaerythritol monomers.

11. The photochromic article of claim 10 wherein the organic host material is a solid transparent homopolymer or copolymer of diethylene glycol bis (allyl carbonate), a thermoplastic polycarbonate, cellulose acetate butyrate, poly(methyl methacrylate), polyvinylbutyral, or a polyurethane.

12. The photochromic article of claim 10 wherein the spironaphthopyran is selected from the naphthopyrans of claim 3.

13. The photochromic article of claim 10 wherein the spironaphthopyran is selected from the naphthopyrans of claim 4.

14. The photochromic article of claim 11 wherein the spironaphthopyran is selected from the naphthopyrans of claim 8.

15. The photochromic article of claim 9 wherein the spironaphthopyran is selected from the naphthopyrans of claim 8.

* * * * *